(12) United States Patent
Evans et al.

(10) Patent No.: US 12,690,603 B2
(45) Date of Patent: Jul. 28, 2026

(54) BEE ANTIVIRAL COMPOSITIONS

(71) Applicant: The United States of America, as represented by the Secretary of Agriculture, Washington, DC (US)

(72) Inventors: Jay D. Evans, Harwood, MD (US); Yanping Chen, Boyds, MD (US); James Tauber, Rockville, MD (US); Evan Palmer-Young, Greenbelt, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 441 days.

(21) Appl. No.: 18/303,165

(22) Filed: Apr. 19, 2023

(65) Prior Publication Data

US 2023/0329284 A1     Oct. 19, 2023

Related U.S. Application Data

(60) Provisional application No. 63/332,435, filed on Apr. 19, 2022.

(51) Int. Cl.
*A61K 31/724* (2006.01)
*A23K 20/163* (2016.01)
*A23K 50/90* (2016.01)

(52) U.S. Cl.
CPC ............ *A23K 50/90* (2016.05); *A23K 20/163* (2016.05); *A61K 31/724* (2013.01)

(58) Field of Classification Search
CPC .................................................. A61K 31/724
See application file for complete search history.

(56) References Cited

U.S. PATENT DOCUMENTS

| | | | |
|---|---|---|---|
| 7,597,912 | B2 | 10/2009 | Probasco et al. |
| 7,922,559 | B2 | 4/2011 | Cook |
| 9,540,642 | B2 | 1/2017 | Inberg et al. |
| 10,022,338 | B2 | 7/2018 | Plettner et al. |
| 10,100,306 | B2 | 10/2018 | Inberg et al. |
| 10,557,138 | B2 | 2/2020 | Gleit-Kielmanowicz et al. |
| 10,813,960 | B2 | 10/2020 | Stamets |
| 10,925,920 | B2 | 2/2021 | Del Vecchio |

OTHER PUBLICATIONS

Kim et al (Scientia Horticulturae 256 (2019) 1086) (Year: 2019).*
Costa et al (Apidologie 41 (2010) 141-150). (Year: 2010).*
LeBlanc et al (J. Agric. Food Chem. 2008, 56, 8565-8573). (Year: 2008).*
EC Palmer-Young, et al., 2017, "Nectar and Pollen Phytochemicals Stimulate Honey Bee (*Hymenoptera: apidae*) Immunity to Viral Infection," J. Econ. Entomol. 110(5): 1959-1972.

(Continued)

*Primary Examiner* — Benjamin J Packard
(74) *Attorney, Agent, or Firm* — John Fado; Maria Restrepo-Hartwig

(57) ABSTRACT

The invention relates to compositions for reducing viral load in bees, the compositions comprising at least one plant secondary metabolite and a carrier comprising at least one sweetener, kits comprising such compositions, and methods of using such compositions to reduce viral load in bees.

19 Claims, 6 Drawing Sheets
(1 of 6 Drawing Sheet(s) Filed in Color)

(56) References Cited

OTHER PUBLICATIONS

JP Tauber, et al., 2020, "Colony-Level Effects of Amygdalin on Honeybees and Their Microbes," Insects 11(11): 783.
JP Tauber, et al., 2019, "Natural Product Medicines for Honey Bees: Perspective and Protocols," Insects 10: 356.
LN Standifer, et al., 1977, "Supplemental Feeding of Honey Bee Colonies," USDA, Agriculture Information Bulletin No. 413.
Bo Sucu, et al., 2019, "Synthesis of Novel Methyl Jasmonate Derivatives and Evaluation of Their Biological Activity in Various Cancer Cell Lines," Bioorg. Chem. 91: 1031-1046.

* cited by examiner

PBS   MJL   MJM   MJH   TL   TM   TH   +C

PBS   MJL   MJM   MJH   TL   TM   TH   +C

BEE ANTIVIRAL COMPOSITIONS

CROSS-REFERENCE TO RELATED APPLICATIONS

This application claims the benefit of U.S. Provisional Application No. 63/332,435 filed Apr. 19, 2022. The contents of this provisional patent application are hereby expressly incorporated by reference in their entirety.

FIELD OF THE INVENTION

The invention relates to compositions comprising at least one downstream plant secondary metabolite, kits comprising such compositions, and methods of using such compositions to reduce viral load in honey bees.

BACKGROUND OF THE INVENTION

Honey bees are required for the effective pollination of crops and are therefore critical to world agriculture. Honey bees also produce economically-important products, including honey and bees wax. The honey bees in America and in Europe are various races of *Apis mellifera*. Other related species used for pollination and honey production worldwide include *Apis cerana, Apis dorsata*, and *Apis florea*.

Challenges to honey bee health arise from disease agents, chemical stress, and nutritional challenges. Diseases and infections in bees arise from many sources, including viruses, bacteria, fungi, protozoa, insects, and mites. Bees are host to a diversity of viral species and strains, such as deformed wing virus (DWV), Israeli acute paralysis virus (IAPV), Kashmir bee virus (KBV), acute bee paralysis virus (ABPV), black queen cell virus (BQCV), Kakugo virus, *Varroa destructor* virus-1 (VDV1), sacbrood virus (SBV), slow bee paralysis virus (SBPV), Lake Sinai virus (LSV), Tobacco ringspot virus (TRSV), Ganda bee virus (GABV), *Apis mellifera* filamentous virus (AmFV), *Osmia cornuta* nudivirus (OcNV), Bee macula-like virus (BeeMLV), chronic bee paralysis virus (CBPV), and Scaldis River bee virus (SRBV).

DWV is a worldwide bee disease often associated with high *Varroa* mite populations. In the absence of *Varroa*, DWV normally persists at low levels within the bee colony with no detrimental effect. The DWV is a member of the *Iflaviridae* family, and can be found in all bee life stages from egg to adult, and in the glandular secretions used to feed larvae and the queen. Isolated from adult deformed bees in 1982 in Japan, DWV was given its name after the symptoms with which it was closely associated.

In general, viruses can be transmitted either via horizontal transmission, where viruses are transmitted among individuals of the same generation, or via vertical transmission, where viruses are transmitted from adults to their offspring. *Varroa* (*Varroa destructor*) mites are the number one parasite of managed honey bees (*Apis mellifera*) and the biggest global threat to commercial beekeeping. In addition to their parasitic effects, *Varroa* mites act as vectors for a number of honey bee pathogens, including DWV, KBV, ABPV, and BQCV. It is well established that DWV, in particular, is a primary cause of winter honey bee colony losses as well as decreased colony growth year-round.

U.S. Pat. No. 10,925,920 relates to nutritional powder compositions for use as nourishment for bees and for the prophylaxis and treatment of acariosis, in particular of *Varroa destructor* infestations. The compositions comprise nutritional and tonic ingredients, such as powdered milk or algae containing vegetal proteins and/or yeasts; sugars and lower organic acids; natural antioxidants and antiseptics contained in the essential extracts of *Origanum vulgare* and *Pelargonium graveolens* or geranium essential oil, and in the essential oils of one or more aromatic or medicinal plants; and substances medicinal to bees, comprising at least one of thymol and extracts of *Thymus vulgaris*, and at least one of oxalic acid, extracts of Aloe vera or Aloe arborescens, geraniol and extracts of *Beta vulgaris* cv. *altissima*, and mixtures of two or more of the same.

U.S. Pat. No. 10,022,338 relates to compounds and methods for treating *Varroa destructor* infection of a bee colony by placing specific chemical compounds in the bee colony enclosure.

U.S. Pat. No. 10,813,960 relates to compositions comprising effective amounts of an ethanol mycelium extract of Inonotus obliquus, *Ganoderma resinaceum, Fomitopsis pinicola, Fomes fomentarius, Schizophyllum commune, Trametes versicolor, Ganoderma* applanatum, or combinations thereof, mixed with one or more bee feeding supplements; and one or more preservatives for improving bee health.

U.S. Pat. No. 10,557,138 relates to methods of reducing viral load or suppressing viral replication in a *Varroa destructor* mite infected by a virus. The method comprises providing to the *Varroa destructor* mite infected by a virus a composition comprising an effective amount of at least one double-stranded RNA (dsRNA).

U.S. Pat. No. 7,922,559 teaches methods for managing a honey bee colony to prevent injury and disease (arising from an insect, a bacteria, a fungi, a virus, a protozoa or a parasite) by administering to honey bees, honey bee larvae, or a honey bee hive, an effective amount of an aqueous composition comprising an aromatic sulfonic acid in its acid form.

U.S. Pat. Nos. 7,597,912 and 10,100,306 relates to methods of controlling a honey bee parasitic mite, the method comprising contacting the parasitic mite with an effective amount of a composition comprising a hop derivative.

U.S. Pat. No. 9,540,642 relate to bee-ingestible, bee-absorbable, mite-ingestible, or mite-absorbable compositions comprising an excipient and a nucleic acid molecule to reduce parasitation of the bee by *Varroa destructor*.

Currently there are registered antibiotics for treating bacterial diseases, and registered chemical treatments for controlling mite and beetle parasites in honey bee colonies. There are no registered products available to beekeepers for controlling viral disease or reducing the impacts of chemical exposure on bee health, controlling fungal infections.

A significant improvement in the survival of bee larvae and the extension of the life span of adult bees would be of great value to the beekeeping industry, allowing more bees to make more trips to gather nectar, pollen, water, and propolis, thus ensuring greater honey production. Accordingly, there is a need in the art for improved compositions and methods for managing bee hives that provide for effective control and treatment of infections, and stress in honey bees.

Thus, new methods and compositions for controlling viral infections in honey bees are needed. The present disclosure fulfills these needs and provides further related advantages.

SUMMARY OF THE INVENTION

Provided herein are methods and compositions for controlling viral infections in bees.

In an embodiment, the invention relates to a composition for reducing viral load in bees comprising at least one plant secondary metabolite and a carrier. In some embodiments, the carrier in the composition comprising at least one plant secondary metabolite and a carrier is an aqueous solution, a syrup, a solid, a spray, a gel, a dough, a granule, a powder, or a combination thereof. In some embodiments, the carrier in the composition comprising at least one plant secondary metabolite and a carrier comprises at least one sweetener. In some embodiments, the at least one sweetener, in the composition comprising at least one plant secondary metabolite and a carrier is a bulk sweetener, a sugar sweetener, a sugar substitute sweetener, an artificial sweetener, a high-intensity sweetener, or a combination thereof. In some embodiments, the sugar sweetener, in the composition comprising at least one plant secondary metabolite and a carrier is a saccharide-containing compound. In some embodiments, the saccharide-containing compound, in the composition comprising at least one plant secondary metabolite and a carrier is a sucrose, a dextrose, a maltose, a lactose, a dextrin, a trehalose, a D-tagatose, a dried invert sugar, a fructose, a levulose, a galactose, corn syrup solids, or a combination thereof. In some embodiments, the at least one plant secondary metabolite in the composition for reducing viral loads in bees is methyl jasmonate, thymol, ferulic acid, octanoic acid, tannin, or a mixture thereof.

In some embodiments, the composition comprising at least one plant secondary metabolite and a carrier further comprises at least one cyclodextrin. In some embodiments, the cyclodextrin in the composition comprising at least one plant secondary metabolite and a carrier is a β-cyclodextrin. In some embodiments, the β-cyclodextrin in the composition comprising at least one plant secondary metabolite and a carrier is methyl-β-cyclodextrin; hydroxypropyl-β-cyclodextrin; or a combination thereof.

In an embodiment, the disclosure relates to a method of reducing viral load in a bee. In some embodiments, the method of reducing viral load in a bee may comprise administering to the bee an effective amount of a composition comprising at least one plant secondary metabolite, at least one cyclodextrin, and a carrier. In some embodiments, the method of reducing viral load in a bee comprises administering to the bee an effective amount of a composition comprising at least one plant secondary metabolite, and a carrier.

In an embodiment, the disclosure relates to a kit comprising at least one plant secondary metabolite and a carrier. In some embodiments, the kit may comprise a blend of at least one plant secondary metabolite, at least one cyclodextrin, and a carrier.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4A shows fluorescent microscope images of treated and control bees where the fluorescence is reflective of net viral load in each bee. FIG. 4B shows images of the same bees shown in FIG. 4A, filtered to remove all background fluorescence. The treatments are shown above the images, where PBS=bees were treated with buffer alone; MJL=bees were treated with low dose of methyl jasmonate; MJM=bees were treated with medium doses of methyl jasmonate; MJH=bees were treated with high doses of methyl jasmonate; TL=bees were treated with low doses of thymol; TM=bees were treated with medium doses of thymol; TH=bees were treated with high doses of thymol; +C=bees were infected with 105 DWV.

DETAILED DESCRIPTION

Figure 1:
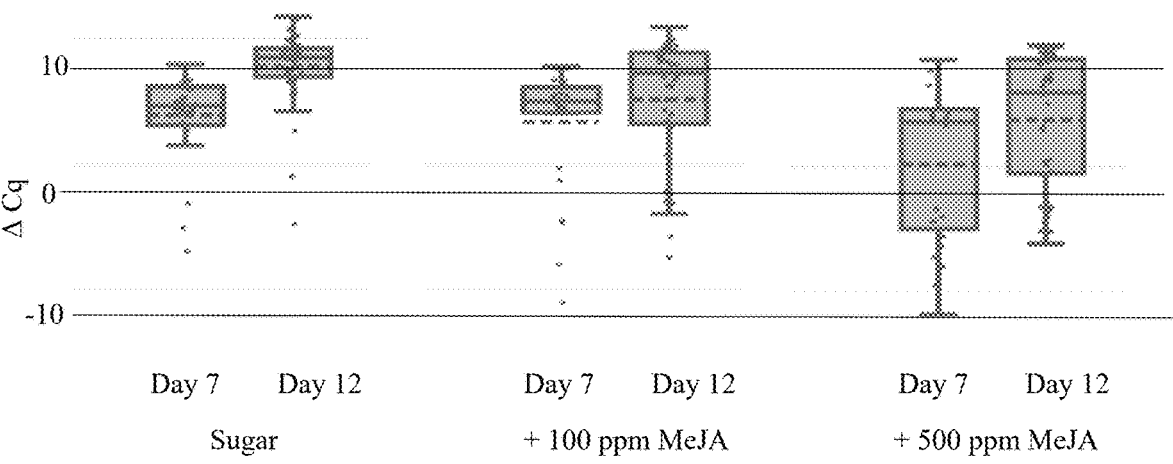
FIG. 1 depicts a graph of the DWV load per bee measured 7 days or 12 days after the start of treatment, quantified using qPCR, and analyzed using the change in quantification cycle values (ACq). Y Axis presents the ACq values. X Axis presents the different compositions fed to the VDV-infected bees: sugar alone (as control), sugar+100 ppm MeJA, or sugar+500 ppm MeJA. Post Hoc Tukey HSD statistical analyses were performed. $P=0.93$ for sugar vs. sugar+100 ppm MeJA at day 7; and $P=0.012$ for sugar vs. sugar+500 ppm MeJA at day 7. $P=0.02062$ for sugar vs. sugar+100 ppm MeJA at day 12; and $P=0.00006$ for sugar vs. sugar+500 ppm MeJA at day 12.

The present invention relates to compositions comprising at least one plant secondary metabolite and a carrier, kits comprising such compositions, and methods of using such compositions to reduce bees' viral load.

Bees are susceptible to a myriad of viral infections. At least 24 different bee viruses have been identified. Most are positive strand RNA viruses, which contain RNA-dependent RNA polymerase (RdRp). Two phylogenetic families of bee viruses with two main structural formats have been identified. The present application now discloses methods and compositions for the treatment of viral infections in bees. The present application further discloses reduction of the viral load in bees by using the treatment taught here.

Plants have evolved many secondary metabolites involved in plant defense, which can be classified into three sub-groups: nitrogen compounds (including alkaloids, cyanogenic glycosides, glucosinolates and benzoxazinoids), terpenoids, and phenolics.

Methyl jasmonate (abbreviated MeJA) is a volatile organic jasmonic acid derivative used by plants in defense, and in many diverse developmental pathways such as seed germination, root growth, flowering, fruit ripening, and senescence. Methyl jasmonate is derived from jasmonic acid in a reaction catalyzed by S-adenosyl-L-methionine: jasmonic acid carboxyl methyltransferase.

Jasmonates are phytohormones involved in a wide range of plant processes, including growth, development, senescence, and defense. It has been shown that Jasmonic acid (JA) crosstalks with other plant hormone signaling in regulating the balance between plant growth and defense response. The jasmonate family comprises jasmonic acid, cis-jasmonate, and methyl-jasmonate, among others. In efforts to reduce the solubility limitations Jasmonic acid derivatives have been produced. Among these are methyl 4,5-didehydrojasmonate; methyl 5, 7, 9, 10-tetrabromojasmonate; 3-((3-methyl-1,2,4-oxadiazol-5-yl)methyl)-2-(pent-2-en-1-yl) cyclopentanol; methyl-5-chloro-4,5-didehydrodihydro-jasmonate; t-butyl 5-chloro-4,5-didehydrodihydro-jasmonate; 4-methyl-3-(2-pentenyl)-2-oxazolidinone; and (3-hydroxy-2-pentylcyclopentyl) acetic acid; methyl 4,5-didehydrojasmonate.

Thymol (2-isopropyl-5-methylphenol) is a natural monoterpenoid phenol derivative of p-Cymene. Thymol is used as a rapidly degrading, non-persisting pesticide, and as a general purpose disinfectant.

Ferulic acid is a hydroxycinnamic acid, an organic compound and a polyphenol with the formula $(CH_3O)HOC_6H_3CH—CHCO_2H$. Classified as a phenolic phytochemical, ferulic acid is an amber colored solid. Esters of ferulic acid are found in plant cell walls, covalently bonded to hemicellulose such as arabinoxylans. Ferulic acid has the ability of stabilizing other antioxidants.

Caprylic acid, also known under as octanoic acid or C8 Acid, is a saturated fatty acid, medium-chain fatty acid. It has the structural formula $H_3C—(CH_2)_6—COOH$), and is a colorless oily liquid that is minimally soluble in water with a slightly unpleasant rancid-like smell and taste. It is used to treat candidiasis and bacterial infections.

Tannins (or tannoids) are a class of astringent, polyphenolic biomolecules that bind to and precipitate proteins and various other organic compounds including amino acids and alkaloids. The tannin compounds are widely distributed in many species of plants, where they play a role in protection from predation (acting as pesticides) and might help in regulating plant growth. Cinnamaldehyde is a phenylpropanoid that is naturally synthesized by the shikimate pathway. Its chemical formula is $C_6H_5CH—CHCHO$ and naturally occurs predominantly in the trans (E) isomer. Rosmarinic acid (3,4-Dihydroxycinnamic acid (R)-1-carboxy-2-(3,4-dihydroxyphenyl)ethyl ester) is a natural antimicrobial compound and polyphenol antioxidant found in many Lamiaceae herbs used commonly as culinary herbs.

The present disclosure is based, in part, on the unexpected finding that plant secondary metabolites exhibit activity against bee viruses. Prior to the present application, it was not taught or suggested that plant secondary metabolites such as jasmonate derivatives, thymol, ferulic acid, octanoic acid, and/or tannin may be effective in reducing viral load in bees. The present disclosure, thus, provides the use of jasmonate derivatives such as MeJA, thymol, ferulic acid, octanoic acid, and/or tannin, either alone or in combination, as highly potent agents for treating viral infections in bees with no or very low levels of side effects on the bees. The inventors have tested over 140 plant secondary compounds triggered as part of plant defenses against insects, microbes, and viruses, identifying compounds that reduce bee viral load, and chemicals that may be possible synergists with MeJA.

A bee administered a composition comprising at least one plant secondary metabolite, and a carrier may be at any stage of the life cycle, it may be an egg, a larva, a pupa, or an adult. It is also possible to administer the composition to the bee hive itself.

In an embodiment, the composition may comprise at least one plant secondary metabolite and at least one of a bulk sweetener, a flavor, a dry-binder, a tableting aid, an anti-caking agent, an emulsifier, an antioxidant, an enhancer, an absorption enhancer, a high intensity sweetener, a softeners, a color, or a combination thereof.

In some embodiments, the at least one sweetener in the composition comprising at least one plant secondary metabolite is a bulk sweetener, a sugar sweetener, a sugar substitute sweetener, an artificial sweetener, a high-intensity sweetener, or a combination thereof.

The at least one bulk sweetener in the composition comprising at least one plant secondary metabolite may be at least one sugar sweetener or at least one non-sugar sweetener. In some embodiments, a sugar sweetener in the composition comprising at least one plant secondary metabolite is a saccharide-containing compound, including, but not limited to, sucrose, dextrose, maltose, lactose, dextrin, trehalose, D-tagatose, dried inverted sugar, fructose, levulose, galactose, corn syrup solids, and the like, or a combination thereof.

The non-sugar sweetener in the composition comprising at least one plant secondary metabolite may be a sugar alcohol. In certain embodiments, the sugar alcohol may be sorbitol, mannitol, xylitol, maltitol, isomalt, erythritol, lactitol, or a combination thereof.

A composition comprising at least one plant secondary metabolite and a carrier may comprise at least one high intensity artificial sweetening agent. The at least one high intensity sweetening agent may be a sucralose, an aspartame, an acesulfame salt, an alitame salt, a saccharin, a saccharin salt, a cyclamic acid, a cyclamic acid salt, a glycyrrhizin, a dihydrochalcone, a thaumatin, a monellin, a stevioside, or a combination thereof.

In an embodiment, the disclosure relates to a method of reducing viral load in a bee by administering to honey bees, honey bee larvae, or honey bee hive an effective amount of a composition comprising at least one plant secondary metabolite and a carrier.

As used herein, the term "treating" includes abrogating, substantially inhibiting, slowing, or reversing the progression of a condition, substantially ameliorating clinical or aesthetical symptoms of a condition, or substantially preventing the appearance of clinical or aesthetical symptoms of a condition. In an aspect according to the present disclosure, a composition may be used to treat an organism or colony of organisms for the effects of parasitization. In an aspect, a composition comprising a plant secondary metabolite may be used to treat a single host organism, several host organisms, or a colony for parasites. In an aspect, the host organism is a bee, and the parasite is a virus.

As used herein, the term "arthropod" refers to both adult and pupa of invertebrate animals having an exoskeleton (external skeleton), a segmented body, and jointed appendages. Arthropods are members of the phylum Arthropoda and includes the insects, arachnids, and crustaceans. Arthropods according to the present disclosure, include but are not limited to *Apis mellifera, Apis cerana, Trigona minima, Halictidae, Bombus* sp., fleas, flies, lice, ticks, mites, and beneficial insects. The present disclosure provides for, and includes, methods and compositions for treating arthropods as either a host or as a parasite or pest.

In an aspect, an arthropod may be an insect. In certain aspects, an insect may be a bee. As used herein, the term "bee" refers to both an adult bee and pupal cells thereof. According to one aspect, the bee is in a hive. An adult bee is defined as any of several winged, hairy-bodied, usually stinging insects of the superfamily Apoidea in the order Hymenoptera, including both solitary and social species, and characterized by sucking and chewing mouthparts for gathering nectar and pollen. Examples of bee species include, but are not limited to, *Apis, Bombus, Trigona, Osmia*, and the like. In one aspect, bees include, but are not limited to, bumblebees (*Bombus terrestris*), honey bees (*Apis mellifera*) (including foragers and hive bees) and *Apis cerana*. The present disclosure provides for, and includes methods and compositions for treating bees as a host for parasites, such as viruses.

According to one aspect, a bee is part of a colony. The term "colony" refers to a population of bees comprising dozens to typically several tens of thousands of bees that cooperate in nest building, food collection, and brood rearing. A colony normally has a single queen, the remainder of the bees being either "workers" (females) or "drones" (males). The social structure of the colony is maintained by the queen and workers and depends on an effective system of communication. Division of labor within the worker caste primarily depends on the age of the bee but varies with the needs of the colony. Reproduction and colony strength depend on the queen, the quantity of food stores, and the size of the worker force. Honey bees can also be subdivided into the categories of "hive bees", usually for the first part of a workers lifetime, during which the "hive bee" performs tasks within the hive, and "forager bee", during the latter part of the bee's lifetime, during which the "forager" locates and collects pollen and nectar from outside the hive, and brings the nectar or pollen into the hive for consumption and storage. The present disclosure provides for, and includes methods and compositions for reducing viral loads in insects colonies.

As used herein, the term "pest" refers to both adult and immature forms of an organism that is invasive or prolific, detrimental, troublesome, noxious, destructive, a nuisance to either plants or animals, or ecosystems. A parasite is a type of pest. It is possible for an organism to be a pest in one setting but beneficial, domesticated, or acceptable in another.

As used herein, the term "parasite" refers to both adult and immature forms of organisms that directly benefit at the expense of another, host organism, for example by feeding on the blood or fluids of the host, living intracellularly in a host organism cell, or living within a body of a host organism. Parasites include organisms that are animals, fungi, bacterial, or plants and are identified by their negative or detrimental interaction with a host. In some embodiments, a parasite as used herein may in turn serve as a host to a second parasite. In some embodiments, a parasite and host may be of the same type of organism (e.g., an arthropod host and an arthropod parasite). Parasites include, but are not limited to, Acari (ticks, mites), Hippoboscoidea (flies), Ichneumonoidea (parasitic wasps), Oestridae (bot flies), Phthiraptera (lice), Siphonaptera (fleas), Tantulocarida, Pea crab, and Sacculina. As used herein, a pest may include both parasitic and non-parasitic life stages. The present disclosure provides for, and includes methods and compositions for treating parasites. In an aspect, the parasite may be a virus.

As used herein, the term "excipient" refers to any inactive substance in a formulation having an active ingredient such as an anti-parasitic, anti-pest, or insecticidal plant secondary metabolite. In some embodiments, an excipient includes substances that may provide additional functionality to a composition comprising at least one plant secondary metabolite. Excipient functions include, but are not limited to "bulking agents," "fillers," "diluents," and "carriers." Bulking up allows convenient and accurate dispensation of compositions of the present disclosure. Excipients can also serve to facilitate ingestion of the compositions by organisms and include various carbohydrates, proteins, fatty acids, pollens, and pollen substitutes. Excipients can also serve to facilitate absorption of compositions by organisms and include, for example, both aqueous and non-aqueous solutions of active ingredients. Non-limiting examples of excipients include corn syrup, sugar syrup, sugar solid, sugar semi-solids, pollen, soy protein, and pollen and protein mixtures. Excipients may further comprise attractants, buffers, and nutrient supplements. Compositions of the present disclosure may be coated with, encapsulated in, dissolved in, mixed with, or otherwise combined with an excipient. As used herein, the term excipient may refer to a mixture of inactive substances.

PCT Publication No. WO 2021011568 discloses the use of compositions comprising one or more cyclodextrins capable of scavenging toxic compounds from honey bees. The compositions may boost the immune defenses of individual honey bees, protecting the entire colony against infectious disease and reducing the effects of pesticide exposure. In an embodiment, the invention provides for a composition comprising at least one jasmonate derivative, a cyclodextrin, and a carrier.

This application provides and discloses compositions comprising an anti-parasitic, anti-pest, or insecticidal composition comprising a at least one plant secondary metabolite and at least one excipient. In an aspect, the excipient can be a combination of one or more inactive components. In some aspects, the excipient comprises a sugar. Exemplary sugars include hexoses, disaccharides, trisaccharides, and higher sugars. Excipient sugars include, for example, fructose, glucose, sucrose, trehalose, lactose, galactose, ribose. In other aspects, the excipient comprises a sugar and a solvent. In other aspects, the excipient comprises a protein. In an aspect, the protein is a soy protein. In other aspects the excipient may be pollen. In aspects according to the present disclosure, the excipient may be a bee food. In some aspects, the excipient comprises Tryptone. In some aspects, the excipient comprises yeast extract. In some aspects, the excipient comprises an essential oil.

Bee feeding is common practice amongst bee-keepers, for providing both nutritional and other, for example, supplemental needs. Bees typically feed on honey and pollen, but have been known to ingest non-natural feeds as well. Bees can be fed various foodstuffs including, but not limited to Wheast (a dairy yeast grown on cottage cheese), soybean flour, yeast (e.g., brewer's yeast, torula yeast), and yeast products products-fed singly or in combination, and soybean flour fed as a dry mix or a moist cake inside the hive, or as a dry mix in open feeders outside the hive. Also useful is sugar, or a sugar syrup. The addition of 10 to 12 percent pollen to a supplement fed to bees improves palatability. The addition of 25 to percent pollen improves the quality and quantity of essential nutrients that are required by bees for vital activity. Cane or beet sugar, isomerized corn syrup, and type-50 sugar syrup are satisfactory substitutes for honey in the natural diet of honey bees. The last two can be supplied only as a liquid to bees. Liquid feed can be supplied to bees inside the hive by, for example, any of the following methods: friction-top pail, combs within the brood chamber, division board feeder, boardman feeder, etc. Dry sugar may be fed by placing a pound or two on the inverted inner cover.

A supply of water must be available to bees at all times. In one aspect, pan or trays in which floating supports-such as wood chips, cork, or plastic sponge-are present are envisaged. Detailed descriptions of supplemental feeds for bees can be found in, for example, USDA publication by Standifer, et al. 1977, entitled "Supplemental Feeding of Honey Bee Colonies" (USDA, Agriculture Information Bulletin No. 413).

In aspects according to the present disclosure an anti-parasitic, anti-pest, or insecticidal composition comprising at least one plant secondary metabolite is combined with an excipient. In an aspect, the composition may be provided as a ratio of at least one plant secondary metabolite to excipient. In an aspect, the ratio may be one-part plant secondary metabolite to 4 parts excipient. In an aspect, the ratio of plant secondary metabolite to excipient may be 1:1, 1:2, 1:5, or 1:10. In other aspects, the ratio of plant secondary metabolite to excipient may be 1:20, 1:25, 1:30, 1:40, or more. In an aspect, ratio of plant secondary metabolite to excipient may be 1:50. In aspects according to the present disclosure, the ratio of plant secondary metabolite to excipient may be determined as a volume to volume (v/v) ratio, or a weight to weight (w/w) ratio. In certain aspects, the ratio may be expressed as a weight to volume (w/v) ratio. In certain aspects, a plant secondary metabolite and an excipient may be a jasmonate derivative and an excipient, may be thymol and an excipient, may be ferulic acid and an excipient, may be octanoic acid and an excipient, may be ferulic acid and an excipient, or may be more than one plant secondary metabolite and an excipient. In certain aspects, a jasmonate derivative and an excipient may be a methyl jasmonate and an excipient.

In aspects according to the present disclosure, the composition may comprise a weight of a plant secondary metabolite combined with an excipient. In an aspect, the plant secondary metabolite may comprise a percentage of the total weight of the composition. In an aspect, the plant secondary metabolite may comprise about 0.1% by weight of the composition. In an aspect, the methyl jasmonate or its derivative may comprise about 0.2% by weight of the composition. In an aspect, the plant secondary metabolite may comprise about 0.3% by weight of the composition. In another aspect, plant secondary metabolite may comprise about 0.4% by weight of the composition. In an aspect, the plant secondary metabolite may comprise up to 0.5% by weight of the composition. In an aspect, the plant secondary metabolite may comprise up to 0.6% by weight of the composition. In an aspect, the plant secondary metabolite may comprise up to 0.7% by weight of the composition. In an aspect, the plant secondary metabolite may comprise up to 0.8% by weight of the composition. In another aspect, plant secondary metabolite may comprise up to 1.0% by weight of the composition. In other aspects, the plant secondary metabolite may comprise up to 1.5% by weight of the composition. In yet other aspects the plant secondary metabolite may comprise up to 2.0% by weight, or 2.5% by weight of the composition.

As used herein, the term "about" is defined as plus or minus ten percent of a recited value. For example, about 1.0 g means 0.9 g to 1.1 g and all values within that range, whether specifically stated or not.

Unless otherwise explained, all technical and scientific terms used herein have the same meaning as commonly understood by one of ordinary skill in the art to which this disclosure belongs.

As used herein, the singular terms "a", "an", and "the" include plural referents unless context clearly indicates otherwise. Similarly, the word "or" is intended to include "and" unless the context clearly indicate otherwise.

Mention of trade names or commercial products herein is solely for the purpose of providing specific information or examples and does not imply recommendation or endorsement of such products.

The term "bee" or "honey bee" interchangeably refers to any species of bee used for performing pollination services including, for example, bees from the genus *Apis* (e.g., *A. mellifera, A. cerana, A. dorsata,* or *A. florea*).

As used herein, the term "beehive" refers to a structure that provides a natural or human-constructed habitation for bees.

As used herein, the term "colony" refers to a singleton or a plurality of bees living in a beehive. For the latter, populations may or may not be comprised of individuals from overlapping generations, and may or may not have an actively reproducing "queen" (i.e., "queen-right").

The term "cyclodextrin" refers to a macrocyclic polysaccharide class of compounds that are typically six-, seven-, or eight-membered rings and contain a hydrophobic core. The optional cyclodextrin component of the inventive composition is an active ingredient and is not an excipient material. Typically, the more monomers in the macrocycle, the larger molecule may be incorporated into an inclusion complex or for sequestration. For example, β-cyclodextrins generally have the correct pore size/gauge to fit tocopherols in an inclusion complex as well as sequester most classes of pesticides. Among other functional characteristics, these compounds typically are capable of binding to, for example, organophosphates (OPs), pyrethroids, formamidine, and neonicotinoid pesticide families (which have some degree of acute, chronic, or sublethal toxicity associated with honey bees). Examples of modified cyclodextrins used in the disclosed invention include methyl-β-cyclodextrin and hydroxypropyl-β-cyclodextrin.

As used herein, the term "carrier" refers to a component of the inventive composition that mimics or supplements naturally occurring nectar the bees would find and use for upkeep of the hive and mixes with the at least one jasmonate derivative and cyclodextrin component. This component may comprise a variety of difference substances that are an attractant and/or phagostimulant (e.g., water, natural or synthetic varieties of nectar, nectar substitutes, sugar granules, sugar dough, sugar solution, sugar substitute, etc.) that is capable of providing the compositions of the invention to the bees in an ingestible form. This component may also include other nutritive or non-nutritive constituents. When the composition of the invention comprises a cyclodextrin, this component preferably does not contain a pollen or pollen substitute to prevent undesirable binding of the cyclodextrin component.

The term "viral load" refers to an amount or number of viruses inside of a bee, and typically is an absolute or relative number of viral particles per bee. This measurement may also include viral replication capacity.

Embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby. All publications, patents, and patent applications mentioned in this specification are herein incorpo-
rated by reference to the same extent as if each individual
publication, patent, or patent application was specifically
and individually indicated to be incorporated by reference.

EXAMPLES

Having now generally described this invention, the same
will be better understood by reference to certain specific
examples, which are included herein only to further illus-
trate the invention and are not intended to limit the scope of
the invention as defined by the claims.

Example 1

Methyl Jasmonate Effect on Viral Load of Infected Bees

The effect on viral load of methyl jasmonate (MeJA)
treatment on virally-infected bees was tested after 7 days
and after 12 days of feeding sugar or sugar+MeJA.

Adult honey bees were reared in cages and fed either
sucrose solution, 100 ppm MeJA dissolved in sucrose solu-
tion, or 500 ppm of MeJA dissolved in sucrose solution.
Bees' genetic material was individually examined by qPCR
for normalized VDV loads at 7 days and 12 days after the
start of MeJA treatment. Standard box plots include a dotted
line that represents the mean, and each point represents an
individual bee from one of various cages per treatment.
VDV was not administered artificially and is from a natural
infection. Levels of DWV-A, a recombinant variant of VDV,
were too low in the specimen for quantification. A higher A
Cq indicates more VDV present in the specimen. For Day 7, As seen in FIG. 1, the mean change in quantification cycle
value of VDV per bee (ACq) measured at day 7 of control
bees (fed sugar alone) was 3.9 (+/−3.5); of bees fed sugar+
100 ppm MeJA was 3.45 (+/−4.8); and of bees fed sugar+
500 ppm MeJA was 0.085 (+/−6.16). These data showed a
11.5% decrease in VDV titers in the bees treated with
sugar+100 ppm MeJA as compared to the control bees (bees
fed sugar alone), and a 97.8% decrease in VDV titers in the
bees fed sugar+500 ppm MeJA when compared to the
control bees. For day 12, the mean ACq was 7.8 (+/−2.8) for
control bees, was 5.2 (+/−4.9) for bees feed sugar+100 ppm
MeJA, and was 3.7 (+/−5.3) for bees fed sugar+500 ppm
MeJA. These data showed a 33.3% decrease in VDV titers
in the bees fed sugar+100 ppm MeJA compared to the
control bees, and a 52.6% decrease in VDV titers in the bees
fed sugar+500 ppm MeJA compared to the control. A Post
Hoc Tukey HSD statistical analysis for the data obtained on
day 7 determined that there were no statistically significant
differences between group means of bees fed sugar alone
and bees fed sugar+100 ppm MeJA (P=0.93), and between
bees fed sugar alone and bees fed sugar+500 ppm MeJA
(P=0.012). A Post Hoc Tukey HSD statistical analysis for the
data obtained on day 12 determined that there is a significant
difference between the bees fed sugar alone and the bees fed
sugar+100 ppm MeJA (P=. 02062), and between the bees
fed sugar and the bees fed sugar+500 ppm MeJA (P=.
00006).

Figure 2:
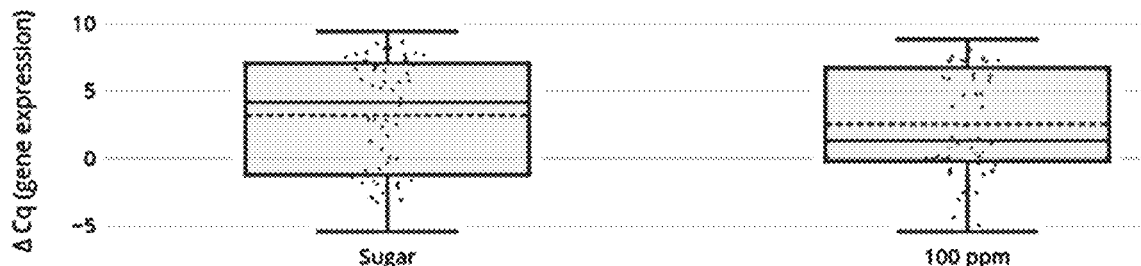
FIG. 2 depicts a graph of the VDV load per bee measured 7 days after the start of treatment, quantified using qPCR, and analyzed using the change in quantification cycle values (ACq). Y Axis presents the ACq values. X Axis presents the different compositions fed to the VDV-infected bees: sugar alone (control), or sugar+100 ppm MeJA.

A second efficiency test was performed where VDV-
infected adult bees were fed 100 ppm of MeJA dissolved in
sucrose solution. As a control, only sucrose solution was
administered. As seen in FIG. 2, the mean ACq at Day 7, was
3.2 (std dev. 4.1; median=4.17) for the control bees fed sugar
alone, and was 2.5 (std dev. 3.8; median=1.33) for bees fed
sugar+100 ppm MeJA. Using the mean, these data show that there was a 21.9% decrease in VDV titers in the bees fed
sugar+100 ppm MeJA compared to the VDV titers of bees
fed sugar alone.

Figure 3:
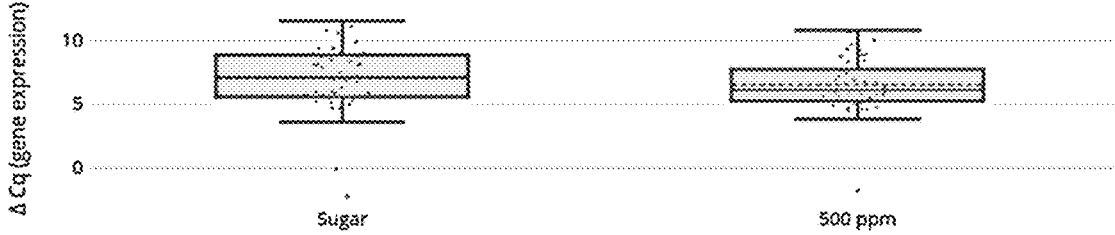
FIG. 3 depicts a graph of the VDV load per bee measured 7 days after the start of treatment, quantified using qPCR, and analyzed using the change in quantification cycle values (ACq). Y Axis presents the ACq values. X Axis presents the different compositions fed to the VDV-infected bees: sugar alone (control), or sugar+500 ppm MeJA.

As seen in FIG. 3, the mean Cq at Day 7 was 7.0 (std dev.
2.5; median=7.1) for the control bees fed sugar alone, and
was 6.5 (2.1; median=6.1) for bees fed sugar+500 ppm
MeJA. Using the mean, these data show that there was a
7.1% decrease in VDV titers in the bees fed sugar+500 ppm
MeJA compared to the VDV titers of bees fed sugar alone.

This Example shows that bees treated for 12 days with
sugar+MeJA present significantly lower viral levels than
bees fed sugar alone.

Example 2

Fluorescent Determination of Effect on Bee Viral Titers

A fluorescent assay was performed to determine the
effects of different treatments on bee viral load.

Bees were treated once with different doses of methyl
jasmonate while simultaneously receiving an effective does
(105 copies) of Deformed wing virus (DWV). The methyl
jasmonte was at low dose (MJL), medium dose (MJM), or
high dose (MJH). Additional bees were treated with thymol
solution in low dose (TL), medium dose (TM), and high
dose (TH). The infective virus dose comprised a viral
construct that expressed nano-luciferase, allowing direct
quantification of viral loads via spectrophotometer. As a
negative control, phosphate buffered saline (PBS) solution
was used alone. As a positive control, bees were infected
with 105 DWV alone. Measurements were repeated nine
times in nine different bees, and an average calculated. Table
1, below, shows the average fluorescence measured across
the different treatments.

TABLE 1

| Average Fluorescence | |
| --- | --- |
| Treatment | Average Counts |
| PBS | 1.687 |
| MJL | 76.120 |
| MJM | 83.905 |
| MJH | 68.246 |
| TL | 67.092 |
| TM | 72.992 |
| TH | 63.290 |
| DWV | 111.366 |

Figure 4A:
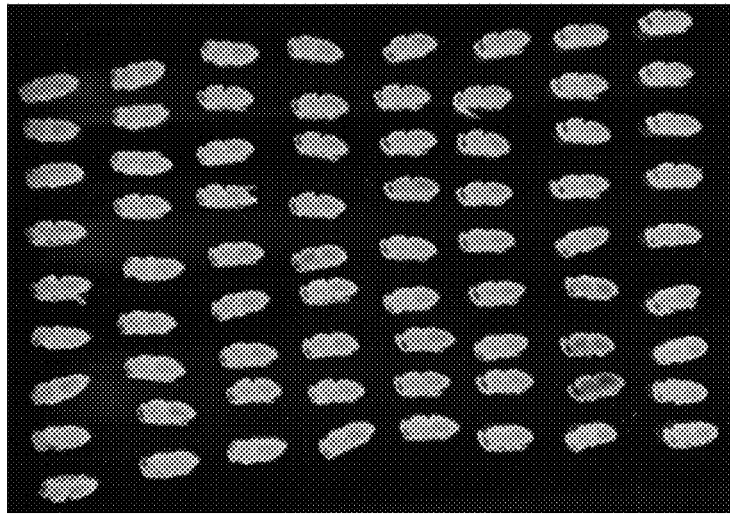
FIG. 4A and FIG. 4B depict images of bees treated with different compounds.
Figure 4B:
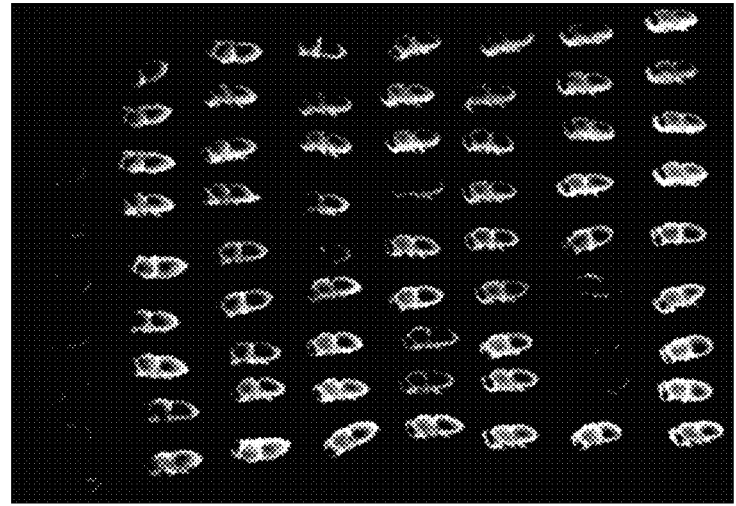

FIG. 4A and FIG. 4B depict Images of bees treated with
different compounds. shows Fluorescent microscope images
of treated and control bees where the fluorescence is reflec-
tive of net viral load in each bee are shown in FIG. 4A.
Images of the same bees, filtered to remove all background
fluorescence are shown in FIG. 4B. The treatments are
shown above the images, where PBS=bees were treated with
buffer alone; MJL=bees were treated with low dose of
methyl jasmonate; MJM=bees were treated with medium
doses of methyl jasmonate; MJH=bees were treated with
high doses of methyl jasmonate; TL=bees were treated with
low doses of thymol; TM=bees were treated with medium
doses of thymol; TH=bees were treated with high doses of
thymol; +C=bees were infected with 105 DWV.

The results obtained in this Example show that DWV-
infected bees treated with either methyl jasmonate or thymol, at low, medium, or high doses have a lower viral load than those treated with PBS alone (DWV).

Example 3

Effect of Other Compounds on Bee Viral Loads

A total of 140 compounds were screened for their effect on bee viral loads.

Figure 5:
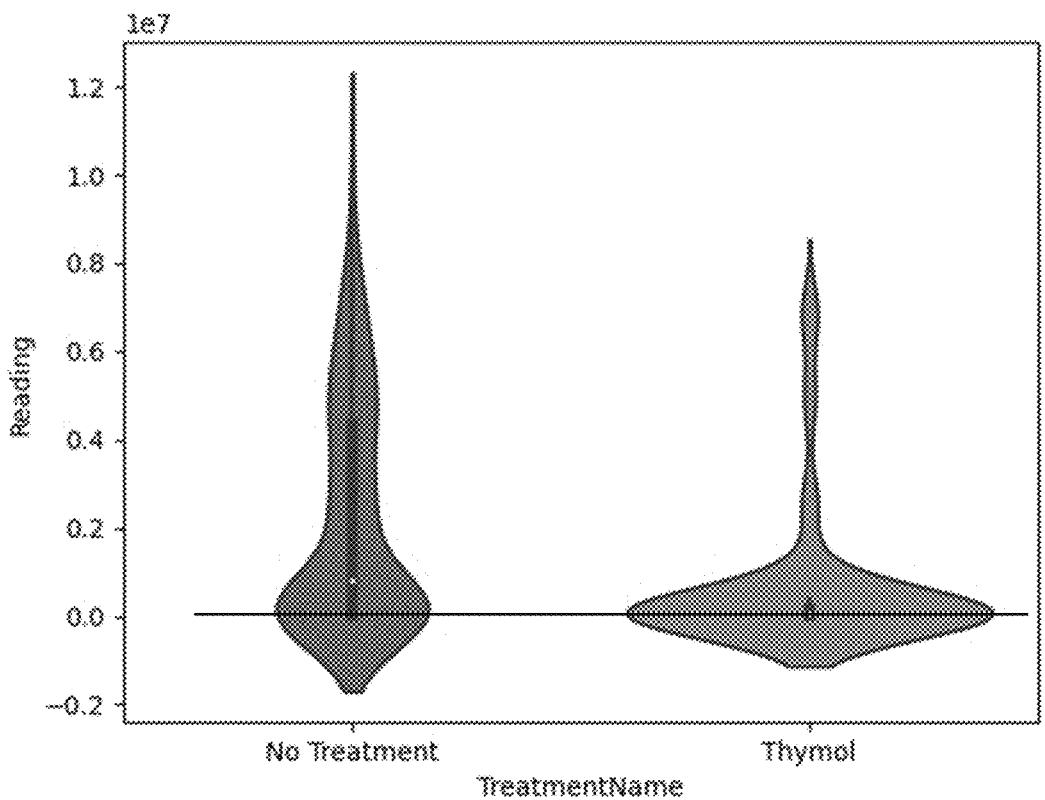
FIG. 5 depicts a graph of the viral levels in bees treated with thymol or control. Horizontal line through the graph marks the threshold for high viral infection. The Y axis presents the values read. The X axis provides the treatment name.

All compounds are selected from food-safe (GRAS, generally recognized as safe by the US FDA) libraries and were tested in live bees to assess adverse impacts to bee health. Trials were carried out using live bees exposed to natural products derived from plants. These trials showed antiviral activity with at least five distinct plant compounds: thymol, ferulic acid (hydroxycinnamic acid), octanoic acid, methyl jasmonate, and tannin. Thymol and octanoic acid blends are being tested to assess possible synergies prior to field trials. Across 3000 honey bee trials, thymol showed a quantitative reduction of high-intensity infections (FIG. 5, those above the red line), suggesting that treatment at the colony level may reduce infection risk and disease.

Figure 6:
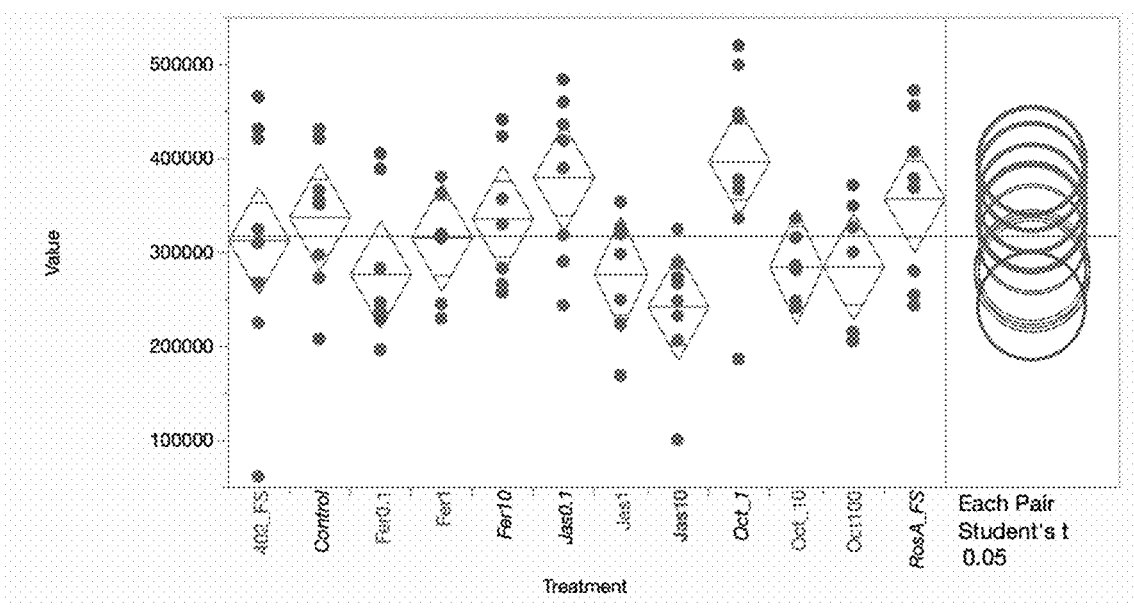
FIG. 6 depicts a graph of the deformed wing virus levels in bees treated with different levels of ferulic acid, methyl jasmonate, or octanoic acid. The Y axis presents the virus levels. The X axis presents the treatments: cinnamaldehyde (402_FS); no added plant secondary metabolite (control); ferulic acid (Fer); methyl jasmonate (Jass); octanoic acid (Oct), or rosmarinic acid (RosA_FS)

As shown in FIG. 6, low levels of ferulic acid (0.1 mM), and higher levels of methyl jasmonate (1 mM or 10 mM) or octanoic acid (10 mM and 100 mM) show a dose response in viral loads.

When used at 10 mM concentrations or lower, the tested compounds had no adverse effects on the survival of honey bee workers. Viral reduction was between 10% and 40% during trials.

We claim:

1. A composition to reduce viral load in bees, the composition comprising at least one plant secondary metabolite, and a carrier comprising at least one sweetener; wherein the at least one plant secondary metabolite is at least about 100 ppm jasmonate ester derivative, at least about 0.1 mM ferulic acid, at least about 0.1 mM octanoic acid, at least about 0.1 mM tannin, or a mixture thereof; wherein the composition optionally comprises at least one cyclodextrin; and wherein ingestion of the composition by bees reduces the viral load in the bees compared to a viral load in bees not ingesting the composition.

2. The composition of claim 1, wherein the carrier is an aqueous solution, a syrup, a solid, a spray, a gel, a dough, a granule, a powder, or a combination thereof.

3. The composition of claim 1, wherein the at least one sweetener is a bulk sweetener, a sugar sweetener, a sugar substitute sweetener, an artificial sweetener, a high-intensity sweetener, or a combination thereof.

4. The composition of claim 3, wherein the sugar sweetener is a saccharide-containing compound.

5. The composition of claim 4, wherein the saccharide-containing compound is a sucrose, a dextrose, a maltose, a lactose, a dextrin, a trehalose, a D-tagatose, a dried invert sugar, a fructose, a levulose, a galactose, corn syrup solids, or a combination thereof.

6. The composition of claim 1, further comprising at least one cyclodextrin.

7. The composition of claim 6, wherein the at least one cyclodextrin is a β-cyclodextrin.

8. The composition of claim 7, wherein the β-cyclodextrin is methyl-β-cyclodextrin; hydroxypropyl-β-cyclodextrin; or a combination thereof.

9. A method of reducing viral load in a bee hive, the method comprising administering to bees, bee larvae, or a bee hive, an effective amount of a composition comprising at least one plant secondary metabolite and a carrier comprising at least one sweetener; the composition optionally comprising at least one cyclodextrin.

10. The method of claim 9, wherein the carrier in the composition is an aqueous solution, a syrup, a solid, a spray, a gel, a dough, a granule, a powder, or a combination thereof.

11. The method of claim 9, wherein the at least one sweetener is a bulk sweetener, a sugar sweetener, a sugar substitute sweetener, an artificial sweetener, a high-intensity sweetener, or a combination thereof.

12. The method of claim 11, wherein the sugar sweetener is a saccharide-containing compound.

13. The method of claim 12, wherein the saccharide-containing compound is a sucrose, a dextrose, a maltose, a lactose, a dextrin, a trehalose, a D-tagatose, a dried invert sugar, a fructose, a levulose, a galactose, corn syrup solids, or a combination thereof.

14. The method of claim 9, wherein the at least one plant secondary metabolite is a jasmonate ester derivative, thymol, ferulic acid, octanoic acid, tannin, or a mixture thereof.

15. The method of claim 9, further comprising at least one cyclodextrin.

16. The method of claim 15, wherein the at least one cyclodextrin is a β-cyclodextrin.

17. The method of claim 16, wherein the β-cyclodextrin is methyl-β-cyclodextrin; hydroxypropyl-β-cyclodextrin; or a combination thereof.

18. A kit for reducing viral load in bees, the kit comprising at least one plant secondary metabolite and a carrier comprising at least one sweetener; wherein the at least one plant secondary metabolite is at least about 100 ppm jasmonate ester derivative, at least about 0.1 mM ferulic acid, at least about 0.1 mM octanoic acid, at least about 0.1 mM tannin, or a mixture thereof wherein the composition optionally comprises at least one cyclodextrin; and wherein ingestion of the composition by bees reduces the viral load in the bees compared to a viral load in bees not ingesting the composition.

19. The kit of claim 18, further comprising at least one cyclodextrin.

\* \* \* \* \*